(12) United States Patent
Michal et al.

(10) Patent No.: US 8,263,170 B2
(45) Date of Patent: Sep. 11, 2012

(54) METHODS FOR IMMOBILIZING ANTI-THROMBOGENIC MATERIAL ONTO A MEDICAL DEVICE OR INTO A COATING THEREON

(75) Inventors: Eugene T. Michal, San Francisco, CA (US); Ni Ding, San Jose, CA (US); Christopher Buchko, Chicago, IL (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 12/683,404

(22) Filed: Jan. 6, 2010

(65) Prior Publication Data

US 2010/0173065 A1 Jul. 8, 2010

Related U.S. Application Data

(62) Division of application No. 09/918,365, filed on Jul. 30, 2001, now Pat. No. 7,682,669.

(51) Int. Cl.
*A61L 33/00* (2006.01)
*B05D 3/00* (2006.01)
*A61F 2/06* (2006.01)

(52) U.S. Cl. ...... 427/2.24; 427/2.1; 427/2.12; 427/2.25; 623/1.42; 623/1.44; 623/1.46; 424/423

(58) Field of Classification Search ............. 427/2.1, 427/2.24, 2.25; 623/1.42, 1.44, 1.46
See application file for complete search history.

(56) References Cited

U.S. PATENT DOCUMENTS

| | | | |
|---|---|---|---|
| 3,688,317 A | 9/1972 | Leonard | |
| 3,914,802 A | 10/1975 | Reick | |
| 4,420,395 A | 12/1983 | Tanihara et al. | |
| 4,478,961 A | 10/1984 | Tanaka et al. | |
| 4,642,242 A * | 2/1987 | Solomon et al. | 427/2.12 |
| 4,834,746 A | 5/1989 | Kira | |
| 5,084,065 A | 1/1992 | Weldon et al. | |
| 5,092,841 A | 3/1992 | Spears | |
| 5,134,192 A * | 7/1992 | Feijen et al. | 525/54.1 |
| 5,232,444 A | 8/1993 | Just et al. | |
| 5,272,012 A | 12/1993 | Opolski | |
| 5,276,015 A | 1/1994 | Khouri et al. | |
| 5,304,121 A | 4/1994 | Sahatjian | |
| 5,336,518 A * | 8/1994 | Narayanan et al. | 427/470 |
| 5,356,433 A | 10/1994 | Rowland et al. | |
| 5,372,719 A | 12/1994 | Afeyan et al. | |
| 5,451,428 A | 9/1995 | Rupp | |
| 5,496,346 A | 3/1996 | Horzewski et al. | |
| 5,507,768 A | 4/1996 | Lau et al. | |
| 5,545,213 A | 8/1996 | Keogh et al. | |
| 5,607,475 A | 3/1997 | Cahalan et al. | |

(Continued)

FOREIGN PATENT DOCUMENTS

EP     914834     5/1999

(Continued)

*Primary Examiner* — Timothy Meeks
*Assistant Examiner* — Cachet Sellman
(74) *Attorney, Agent, or Firm* — Squire Sanders (US) LLP

(57) ABSTRACT

The present invention is directed to a medical device having a polymerized base coat layer for the immobilization of an anti-thrombogenic material, such as heparin, thereon. The binding coat layer is comprised of various chemically functional groups which are stable and allow for the immobilization of the anti-thrombogenic material thereto. Methods for immobilizing the anti-thrombogenic material within the base coat layer posited on a surface of the medical device are also provided.

12 Claims, 1 Drawing Sheet

U.S. PATENT DOCUMENTS

| | | | |
|---|---|---|---|
| 5,618,298 | A | 4/1997 | Simon |
| 5,620,738 | A | 4/1997 | Fan et al. |
| 5,624,411 | A | 4/1997 | Tuch |
| 5,836,962 | A | 11/1998 | Gianotti |
| 5,858,990 | A | 1/1999 | Walsh |
| 5,865,723 | A | 2/1999 | Love |
| 5,876,433 | A | 3/1999 | Lunn |
| 5,879,697 | A | 3/1999 | Ding et al. |
| 5,891,506 | A | 4/1999 | Keogh |
| 6,096,525 | A | 8/2000 | Patnaik |
| 6,099,562 | A | 8/2000 | Ding et al. |
| 6,132,462 | A | 10/2000 | Li |
| 6,193,746 | B1 | 2/2001 | Strecker |
| 6,221,425 | B1 | 4/2001 | Michal et al. |
| 6,245,753 | B1 | 6/2001 | Byun et al. |
| 6,287,285 | B1 | 9/2001 | Michal et al. |
| 6,358,557 | B1 | 3/2002 | Wang et al. |
| 6,465,588 | B1 | 10/2002 | Li |
| 6,541,116 | B2 | 4/2003 | Michal et al. |
| 6,656,517 | B2 | 12/2003 | Michal et al. |
| 6,821,948 | B1 * | 11/2004 | Braun et al. .......... 514/1.2 |
| 7,077,860 | B2 | 7/2006 | Yan et al. |
| 7,682,669 | B1 | 3/2010 | Michal et al. |
| 7,820,190 | B2 | 10/2010 | Hossainy et al. |
| 2001/0020011 | A1 | 9/2001 | Mathiowitz et al. |
| 2001/0051608 | A1 | 12/2001 | Mathiowitz et al. |
| 2002/0004101 | A1 | 1/2002 | Ding et al. |
| 2002/0009535 | A1 | 1/2002 | Michal et al. |
| 2002/0062148 | A1 | 5/2002 | Hart |
| 2002/0087123 | A1 * | 7/2002 | Hossainy et al. .......... 604/198 |
| 2002/0091433 | A1 | 7/2002 | Ding et al. |
| 2002/0120326 | A1 | 8/2002 | Michal |
| 2003/0028243 | A1 | 2/2003 | Bates et al. |
| 2003/0028244 | A1 | 2/2003 | Bates et al. |
| 2003/0036794 | A1 | 2/2003 | Ragheb et al. |
| 2003/0086957 | A1 | 5/2003 | Hughes et al. |
| 2003/0138487 | A1 | 7/2003 | Hogan et al. |
| 2006/0014720 | A1 | 1/2006 | Hossainy et al. |
| 2006/0178738 | A1 | 8/2006 | Yan et al. |

FOREIGN PATENT DOCUMENTS

| | | |
|---|---|---|
| WO | WO 99/38546 | 8/1999 |

* cited by examiner

METHODS FOR IMMOBILIZING ANTI-THROMBOGENIC MATERIAL ONTO A MEDICAL DEVICE OR INTO A COATING THEREON

CROSS-REFERENCE TO RELATED APPLICATIONS

This application is a divisional of U.S. application Ser. No. 09/918,365, filed Jul. 30, 2001, and issuing as U.S. Pat. No. 7,682,669 B1 on Mar. 23, 2010, which is incorporated by reference as if fully set forth, including any figures, herein.

BACKGROUND OF THE INVENTION

This invention relates generally to coatings having an anti-thrombogenic material immobilized thereon a surface area of various medical devices in order to prevent acute thrombogenesis, and is particularly useful when applied to intravascular stents. It is recognized that the present invention is not limited to intravascular stents and rather may be used on various other medical devices where the same principles are applicable.

Stents are implanted within vessels in an effort to maintain the patency thereof by preventing collapse and/or impeding restenosis. Implantation of a stent is typically accomplished by mounting the stent on the expandable portion of a balloon catheter, maneuvering the catheter through the vasculature so as to position the stent at the treatment site within the body lumen, and inflating the balloon to expand the stent to engage the lumen wall. The stent plastically deforms into an expanded configuration allowing the balloon to be deflated and the catheter to be removed to complete the implantation procedure. The use of self-expanding stents obviates the need for a balloon delivery device. Instead, a constraining sheath that is initially fitted about the stent is simply retracted once the stent is in position adjacent the treatment site.

A significant concern associated with the implantation of a stent within the vasculature is the potential for restenosis and thrombogenesis which may in fact be exacerbated by the presence of the stent. The pressure exerted by the stent on the vessel wall may increase the trauma that induces hyperplasia and the presence of the stent in the blood stream may induce a local or even systemic activation of the patient's hemostasis coagulation system. Bound proteins of blood plasma, principally the adhesive proteins such as albumin, fibronectin, fibrinogen and fibrin, are known to trigger coagulation. The result is typically the adhesion and aggregation of thrombocytes on the surface of the stent. These proteins include peptide structures, e.g. the RGD-peptides composed of amino acids, such as glycine, arginine and asparagine. The same structures are involved in the adhesion of thrombocytes as a consequence of receptors of the thrombocyte surface, e.g. collagen, von WilleBrand factor and fibrin interactions. The same result may arise with other biomaterials, generally of metal or plastic composition, which are inserted temporarily or implanted permanently in the patient. The deposit of blood clots on the surface of the biomaterial can result from a complex reaction of plasmatic and cellular mechanisms of coagulation that enhance and influence each other. Thus, the implantation of a stent to keep the lumen of the artery open may only hasten re-occlusion by promoting localized blood clotting and reactive inflammation. Indeed, studies indicate that stents and other untreated biomaterials can be covered with a relatively thick thrombus formation only minutes after contact with blood.

Various pharmacological agents have heretofore been used to address the problem both on a systemic as well as localized level. The latter approach is most often preferred and it has been found convenient to utilize the implanted stent for such purpose wherein the stent serves both as a support for the lumen wall as well as a delivery vehicle for the pharmacological agent. However, the metallic materials typically employed in the construction of stents in order to satisfy the mechanical strength requirements are not generally capable of carrying and releasing drugs. On the other hand, while various polymers are known that are quite capable of carrying and releasing drugs, they generally do not have the requisite strength characteristics. Moreover, the structural and mechanical capabilities of a polymer may be significantly reduced as such polymer is loaded with a drug. A previously devised solution to such dilemma has therefore been the coating of a stent's metallic structure with a drug carrying polymer material in order to provide a stent capable of both supporting adequate mechanical loads as well as carrying and delivering drugs.

Various pharmacological agents have previously been employed to reduce or suppress thrombogenesis and various methods have been developed to load such pharmacological agents onto a stent in order to achieve the desired therapeutic effect. However, further improvement is desired both in terms of the anti-thrombogenic efficacy of materials that can be coated onto stents as well as the methods by which such materials are coated onto the stent. The present invention satisfies these and other needs.

SUMMARY OF THE INVENTION

The present invention overcomes the shortcomings of the prior art methods for imparting anti-thrombogenic characteristics to an implantable medical device, such as a stent, and more particularly provides new methods for covalently immobilizing an anti-thrombogenic material, such as heparin in one of its various chemical forms, within a polymerized base coat layer posited on a surface of the stent. Heparin has been proven to be resistant to thrombosis when used on the surface of an implantable medical device. The immobilization of heparin on different material surfaces, particularly on metal, has for some time presented significant challenges to stent manufacturers. This has been the case because of the highly hydrophilic nature of unmodified heparin which results in the coating being quickly washed away in the bloodstream. Heparin that is ionically bound converts heparin to a lipophilic complex. Coatings having ionically bound heparin or a mixture of ionically bound heparin and polymer increase the retention of heparin on the device surface. This is a somewhat limited improvement as within hours, most heparin will be lost. The covalent attachment of heparin to the device surface, however, tends to withstand a longer time challenge in the blood. As set forth in the present invention, new methods for covalently immobilizing heparin within the polymerized base coat layer posited on the device surface are advantageous in that such methods will help to eliminate SAT and significantly lower the restenosis rate. The resulting stent is deployed at the treatment site to simultaneously provide mechanical support to the lumen wall as well as to reduce the occurrence of thrombogenesis.

In one embodiment, a base coat is applied to the surface of the device and the anti-thrombogenic material is immobilized thereon through a Schiff base reaction. The term "immobilize" as used herein refers to the attachment of the anti-thrombogenic material directly to a support member through at least one intermediate component. A general base coat mixture used in accordance with the present invention includes a binding material, a grafting material, a photoinitiator, and a solvent. Polymerization of the grafting material is carried out by irradiating the base coated device with ultraviolet (UV) light. The binding material of the base coat layer and the anti-thrombogenic material immobilized thereon have chemically functional groups capable of binding to one another in order for the anti-thrombogenic material to be securely bound to the medical device. Immobilization of heparin is achieved by reacting an aqueous heparin solution with a chemically functional group, such as an aldehyde compound, of the base coat layer on the surface of the medical device for an extended period of time.

In another embodiment, immobilization of the anti-thrombogenic material occurs through end-binding heparin in a Schiff base reaction on the surface of the medical device. Specifically, this is achieved by reacting amine-terminated heparin with chemically functional groups of the base coat layer for an extended period of time. Alternatively, heparin is immobilized on the surface of the medical device with spacer groups. Following polymerization of the grafting material of the base coat layer, amine-terminated polyethylene glycol is first reacted with chemically functional groups of the base coat layer, rinsed with water, and then reacted with unfractionated heparin and a water-soluble carbodiimide to form an amide linkage for the immobilization of heparin with spacer groups. Another alternative embodiment includes the immobilization of a mixed population of polyethylene glycol and heparin onto the device surface. Using the standard cinnamaldehyde base coat, the medical device is then immersed into a coupling solution of heparin and polyethylene glycol at various concentrations to react with the chemically functional groups of the base coat layer for an extended period of time.

In other embodiments of the present invention, immobilization of heparin to the base coat layer is achieved by adding a surfactant bound heparin to the base coat. An amine group on the heparin chain may react and then bind to the aldehyde group from cinnamaldehyde to allow for the complete immobilization of the anti-thrombogenic material. Further, the use of carbodiimide chemistry to graft a specific chemical compound to the heparin chain can be employed to achieve immobilization of the carbodiimide-reacted anti-thrombogenic material there to the base coat layer of the medical device.

These and other features and advantages of the invention will become apparent from the following detailed description, taken in conjunction with the accompanying drawings, which illustrate, by way of example, the features of the invention.

DETAILED DESCRIPTION OF THE PREFERRED EMBODIMENTS

The coated medical device of the present invention serves to support the walls of a body lumen while preventing the formation of thrombi thereon. The present invention is not limited to any particular stent configuration or delivery method nor is the construction of the stent structure limited to the use of any particular construction material. For illustration purposes, the following exemplary embodiments are limited to intraluminal stents. However, it is recognized that the present invention is not limited to such applications and rather may be used on various other medical devices where the same principles are applicable.

Figure 1:
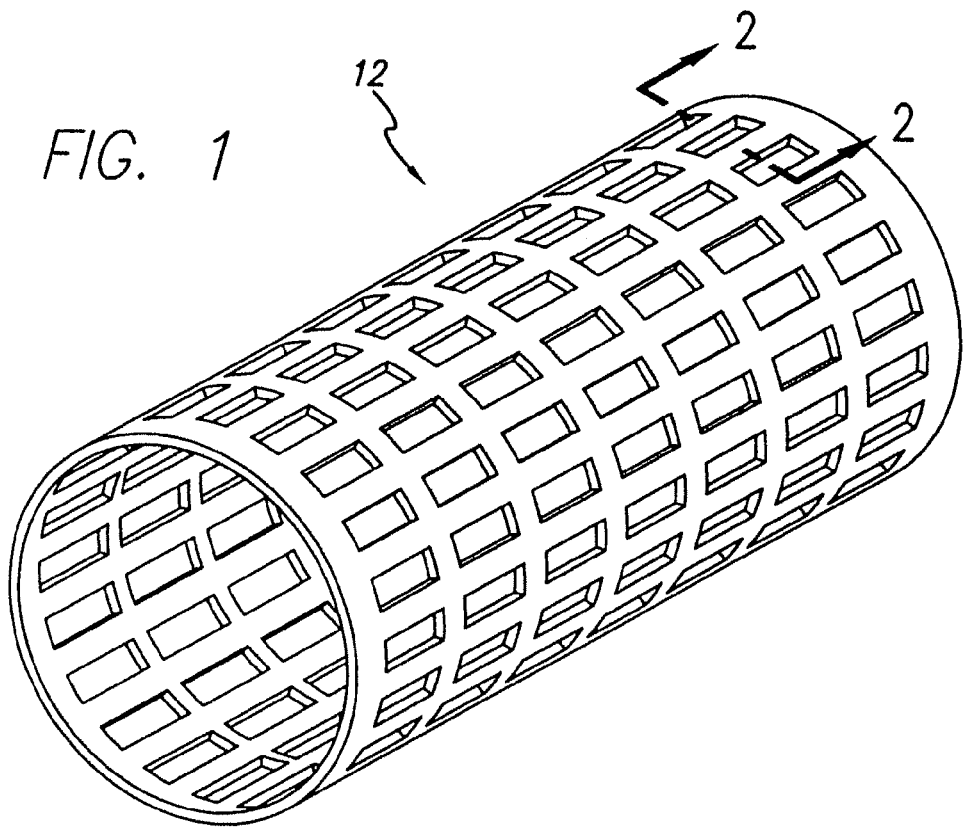
FIG. 1 is a perspective view of a coated stent of the present invention.

FIG. 1 generally illustrates a coated stent 12 of the present invention. The particular stent shown is for illustrative purposes only as virtually any stent configuration can be coated in accordance with the present invention. In fact, the coating can be applied to any device to be implanted or introduced into the body. The coating does not interfere with the stent structure or construction in any way and does not affect its deployment. All known stent designs with attendant delivery systems can benefit from the coating of the present invention.

Figure 2:
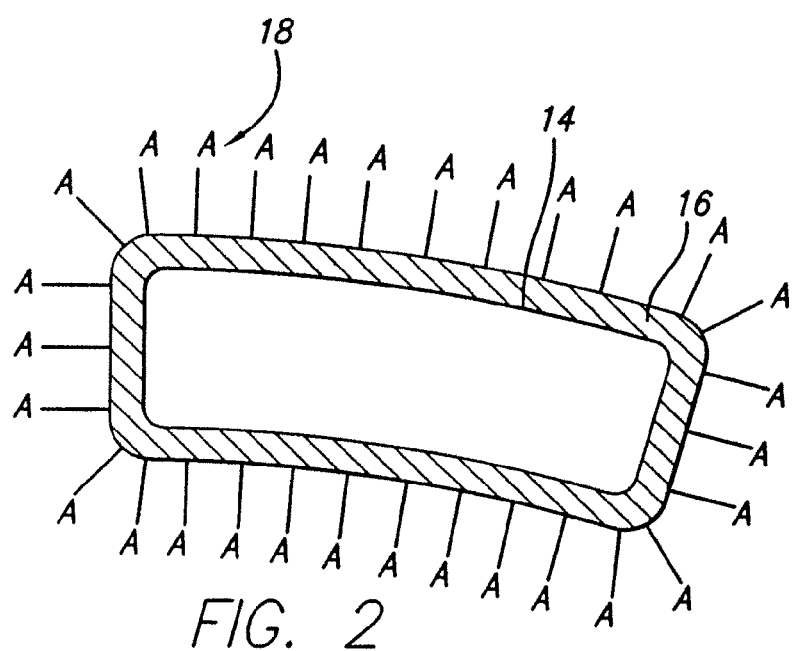
FIG. 2 is an enlarged cross-sectional view taken along lines 2-2 of FIG. 1.

FIG. 2 is an enlarged cross-sectional view of a portion of the stent shown in FIG. 1 and illustrates a base coat layer 16 applied to the stent with the anti-thrombogenic material 18 immobilized thereon in accordance with the present invention. The letter "A" represents the immobilization of the anti-thrombogenic material into the base coat layer of the medical device. The base coat layer 16 is applied directly to all of the stent surfaces 14 including all of its edges. The base coat layer 16 is formed from the polymerization of a base coat mixture which includes a binding material, a grafting material, a photoinitiator, and a solvent. The binding material of the base coat layer 16 and the anti-thrombogenic material 18 (e.g., heparin) immobilized thereon have chemically functional groups capable of binding to one another so that the anti-thrombogenic material will be securely bound to the medical device through the immobilization of covalently bound heparin to the binding material. Heparin is just one example of an anti-thrombogenic material that can be immobilized or coupled onto the surface of the medical device as other glycosaminoglycans such as chondroitin sulfate, dermatan sulfate, and hyaluronate can also be immobilized onto the surface using the same or similar chemistry as set forth below. The term "immobilize" as used herein refers to the attachment of the anti-thrombogenic material directly to a support member through at least one intermediate component.

In one embodiment, the binding material of the base coat is selected from the group consisting of polyazairidine resin compounds, polycarbo-diimide resin compounds, aldehyde compounds, oxirane compounds, acetoacetoxy compounds, and isocyanate compounds. The binding material of the base coat is used to strongly bind to both the anti-thrombogenic material and the grafting material. Preferred polyazairidine compounds used in the present invention include tri-aziridine oligomer, such as Zenaca cs-100™ available from Zeneca Resins. Exemplary of the carbodiimide compounds are XL-29SE™ available from Union Carbide. Exemplary of the aldehyde compounds are glutaraldehyde, cinnamaldehyde, and acrolein. Exemplary of the oxirane compounds are glycidyl methacrylate. Exemplary of the acetoacetoxy compounds are acetoacetoxy ethyl methacrylate. Exemplary of the isocyanate compounds are an aliphatic or aromatic isocyanate monomer, biuret or isocyanurate oligomer, isocyanato ethyl methacrylate or allyl isocyanate, or polyol or polyamine chain extended variant of such starting materials as 1,6 hexamethylene diisocyanate, isophorone diisocyanate, toluene diisocyanate, diphenylmethane-diisocyanate, or bis(4-isocyanato cyclohexyl)methane. In addition, the isocyanate compound can be the monomer or polymer made from allyl isocyanate or other such monomers.

The grafting material of the base coat 16 is selected from the group consisting of vinyl compounds, acrylate compounds, and allyl compounds, such as any oligomer or monomer with one or more vinyl, acrylate or allyl double bonds. The grafting material is used to graft to the device surface and cross-link with the binding material to form the base coat layer. Preferred vinyl compounds used in the present invention include di-vinyl benzene, n-vinyl pyrrolidone, and triethylene glycol divinyl ether. Exemplary of the acrylate compounds are tri-methylol propane tri-acrylate, pentaerythritol tetra-acrylate, and Bisphenol A. ethoxylate diacrylate. Exemplary of the allyl compounds are allyl ether, di-allyl maleate, and tri-allyl isocyanurate.

An example of a general base coat mixture which forms the base coat layer, as shown in FIG. 2, after polymerization of the grafting material on to the device surface, consists of the following chemical compounds, each listed with its respective weight in grams (g), used in accordance with the present invention:

| | |
|---|---|
| Urethane-acrylate (available from Cognis 6892 ™, formerly Henkel 12-892 ™ or equivalent) | 0.01-1.20 g |
| Heterodifunctional monomer | 0.10-1.20 g |
| Benzophenone | 0.001-0.5 g |
| Hydroxycyclohexyl phenyl ketone | 0.001-0.5 g |
| Cellulose acetate butyrate | 0.00-1.00 g |
| Ethyl acetate | 3.00-200 g |
| n-butyl acetate | 3.00-200 g |

The heterodifunctional monomers that may be used in accordance with the invention include, but are not limited to, cinnamaldehyde (aldehyde binding), glycidyl methacrylate (oxirane binding), acetoacetoxy ethyl methacrylate (acetoacetoxy binding), isocyanato ethyl methacrylate or allyl isocyanate (isocyanate binding).

With continued reference to FIGS. 1 and 2, the method for immobilizing the anti-thrombogenic material 18, such as heparin in one of its various forms (e.g., amine-terminated heparin, unfractionated or N-partially desulfated heparin), into a coating posited on the surface of the medical device of the present invention comprises, applying to the medical device a base coat mixture formed from a binding material, a grafting material, a photoinitiator, and a solvent, and polymerizing the grafting material to enable the grafting material to graft to the device and cross-link with the binding material to form the base coat layer 16. The device coated with the base coat layer 16 is typically dried, either at room temperature or elevated temperatures, to enable for the evaporation of the base coat solution solvent. Many suitable solvents may be used in the base coat mixture, including but not limited to water, alcohols, and ketones. Preferred common solvents used in the mixture of the base coat include ester solvents, such as ethyl acetate and butyl acetate, and ketones, such as MEK and MIBK. Aromatics and glycol ethers may also be used as common solvents.

Polymerization of the grafting material is performed by irradiating the device coated with the base coat layer with ultra-violet (UV) light for approximately eight to ten minutes. The process of UV cross-linking or curing is well known in the art and can be executed by a number of various methods. One type of UV source that can be used includes medium pressure mercury bulbs. With the use of UV light, it is essential that photoinitiators be present in the base coat mixture. Photoinitiators are chemicals that absorb UV light energy and produce free radicals which cause a chemical chain reaction for curing. Upon exposure to UV light of the correct wavelength, the photoinitiator is converted to an unstable free radical. This radical will quickly react with chemically functional groups of the base coat mixture to enable the grafting material to graft to the device and cross-link with the binding material. Specifically, during the irradiation process, the acrylate, vinyl or allyl compounds of the grafting material, cross-link to the functional groups of the binding material, i.e., polyaziridine resin, polycarbodiimide resin, aldehyde, oxirane, acetoacetoxy, and isocyanate compounds. The result is a sufficiently adhered base coat layer which contains free unreacted binding component functional groups on the surface of the coating available to immobilize the anti-thrombogenic material (i.e., heparin) thereon. Preferred photoinitiators used in the base coat of the present invention include benzophenone, benzoin methyl ether, 2,2 dimethoxy-2-phenylacetophenone, 1-hydroxycyclohexyl phenyl ketone, and ethyl 4-(dimethylamino)benzoate.

In another embodiment of the present invention, following polymerization of the grafting material from the base coat layer as set forth above, the anti-thrombogenic material is immobilized on the device surface in a Schiff base reaction. Specifically, an aqueous heparin solution of either unfractionated or N-partially desulfated heparin is reacted with the aldehyde groups of the base coat layer for approximately eighteen to twenty-four hours at a temperature in the range of 15° C. to 80° C. and about pH 7.0. At the end of this reaction, the heparin solution is completely immobilized into the base coat layer of the device.

In another embodiment, subsequent to the polymerization of the grafting material from the base coat layer by the same procedure set forth above, the anti-thrombogenic material is end-immobilized in a Schiff base reaction with the chemically functional groups of the base coat layer. The term "end-immobilized" as used herein refers to the attachment of the amine groups on the end of the heparin chain directly to a support member through at least one intermediate component. Specifically, the end immobilization of heparin is achieved by reacting amine-terminated heparin, available from Celsus Lab, with the aldehyde groups of the base coat layer for approximately eighteen to twenty-four hours at a temperature in the range of 15° C. to 80° C. and about pH 7.0. As a result, heparin is completely immobilized into the base coat layer of the device.

In yet another embodiment, following polymerization of the grafting material from the base coat layer as set forth above, the chemically functional groups of the base coat layer are reacted with excess amine-terminated polyethylene glycol (PEG), i.e., PEG($NH_2$)$_2$ (Fluka #14499) having molecular weight (MW) 3400, for approximately eighteen to twenty-four hours at a temperature in the range of 15° C. to 80° C. and about pH 7.0. Other molecular weights of PEG can be used including those in the range of MW 500 to 10,000 (unavailable as standard catalog items). The concentration of PEG ($NH_2$)$_2$ can range from about 0.01 mg/ml to 20 mg/ml. Immediately after the reaction, the base coat layer is rinsed with distilled water. Thereafter, unfractionated heparin is reacted on the device surface with amine-terminated PEG, i.e., PEG ($NH_2$)$_2$, through carbodiimide chemistry to form an amide linkage. A water-soluble carbodiimide, i.e., 1-(3-dimethylaminopropyl-3-ethylcarbodiimide) with a concentration of about 4.0 to 8.0 mg/ml, may be used at a pH of about 4.5 to 7.5 for two to six hours at about room temperature. Subsequent to both reactions, heparin is completely immobilized into the base coat layer of the device. Other chemicals functioning similar to PEG that can be a substitute for include hyaluronic acid, polyvinyl pyrrolidone (PVP) and other hydrogel type materials.

In another embodiment, subsequent to polymerization of the grafting material from the base coat layer (using standard cinnamaldehyde base coat) as set forth above, the chemically functional groups of the base coat layer are reacted with a coupling solution of heparin and alpha hydroxy, beta amino-Poly(ethylene glycol) [OH-PEG-$NH_2$] (Shearwater

2V3F0F02) having a concentration of about 0.01 mg/ml to 20 mg/ml. The reaction between the base coat layer and the coupling solution can occur at all possible ratios of PEG to heparin (e.g., from 0% PEG, 100% heparin to 100% PEG, 0% heparin) for about eighteen to twenty-four hours at a temperature in the range of 15° C. to 80° C. and about pH 8.0. Preferably, the coupling of PEG and heparin to the device surface is reacted at a temperature of about 55° C. A mixed population of PEG and heparin is completely immobilized to the device surface following the above reaction.

In another embodiment, a surfactant bound heparin, such as benzalkonium heparin or TDMA-heparin, is added to the base coat mixture. An amine group on the heparin chain reacts and binds to the aldehyde group of cinnamaldehyde. The reaction between the surfactant bound heparin and the binding material of the base coat runs for about eighteen to twenty-four hours at a temperature in the range of 15° C. to 80° C. and about pH 7.0. Additionally, the base coat mixture can be prepared without a monomer through the use of free unreacted acrylate groups on the device surface.

In another alternative embodiment of the present invention, Superoxide dismutase mimetic (SODm) (available from MetaPhor Pharmaceuticals) can be grafted to the base coat with heparin to provide a covalently attached mixed population of heparin and SODm. SODm catalytically eliminates the superoxide anion radical, reducing oxidative stress. Accordingly, a synergistic effect with heparin can be achieved. The general base coat mixture set forth above using cinnamaldehyde as the heterodifunctional monomer is applied to the device surface by spraying and cured by using medium pressure mercury bulbs for about eight to ten minutes. The device is then immersed in an aqueous solution of heparin (Sigma H-9266) at 7 mg/ml and SODm at 1 mg/ml, adjusted to pH of about 8.0. The coupling reaction is carried out at a temperature in the range of 15° C. to 80° C. for approximately twenty hours. Subsequently, the device surface is rinsed in distilled water and immersed in an 8 mM solution of sodium cyanoborohydride (Aldrich) in pH 7.0 phosphate buffer for approximately twenty-four hours at room temperature. This second reaction reduces the Schiff base to a more stable secondary amine linkage. Thus, a grafted mixed population of SODm and heparin is achieved.

The alternative embodiment in the foregoing involving the covalent attachment of a mixed population of heparin and SODm is further illustrated by the following example. The general base coat mixture using cinnamaldehyde as the heterodifunctional monomer is applied to the device surface and cured by medium pressure mercury bulbs for about eight to ten minutes. The device is then immersed in an aqueous solution of heparin (Sigma H-9266) at 7 mg/ml and SODm at 1 mg/ml, adjusted to pH of about 8.0. The coupling reaction is carried out at a temperature in the range of 15° C. to 80° C. for approximately twenty hours. The heparin coupled device is then rinsed with distilled water and immersed in 8 mM sodium cyanoborohydride in pH 7.0 phosphate buffer for approximately twenty-four hours at room temperature to reduce the Schiff base. An EDC [1-(3-Dimethylaminopropyl)-3-ethylcarbodiimide HCl] mediated coupling between carboxyl groups on heparin and the primary amine group of SODm to yield an amide linkage is executed as follows. Separate solutions of 1 mg/ml SODm in 0.1M MES [4-morpholineethane sulfonic acid monohydrate]/KOH buffer, pH 7.0, and an 8 mg/ml EDC solution in 0.1M MES/KOH buffer, pH 7.0, are prepared. Equal volumes of the SODm and EDC solutions are mixed and the heparin coupled device is then immersed for approximately four hours at room temperature. After the reaction, the device surface is rinsed with distilled water.

One method of coating the device with the base coat mixture is by spray coating. However, the device may be coated by various alternative methods, including but not limited to, dip coating at a given rate, wipe coating, or other suitable techniques known in the art.

In one of the embodiments, the device is an intraluminal stent. As set forth above, however, the present invention is not limited to any particular stent configuration or delivery method. Generally, the surface of the device is cleaned prior to coating, and, although optional, may also be plasma treated in order to improve coating adhesion. Alternatively, a primer coat can be optionally applied to the device surface prior to the application of the base coat layer to improve adhesion of the base coat. Exemplary of the primers that can be used include parylene, primacor (a copolymer of ethylene and acrylic acid), and EVAL™ (a copolymer of ethylene and vinyl alcohol).

As shown in FIGS. 1 and 2 of the presently preferred embodiment, the base coat layer 16 is applied to the entire surface of the intraluminal stent. The coating, 30 however, may be applied to less than the entire outer surface of the stent.

While a particular form of the invention has been illustrated and described, it will also be apparent to those skilled in the art that various modifications can be made without departing from the scope of the invention. Accordingly, it is not intended that the invention be limited except by the appended claims. The following examples further illustrate the present invention. Other biological agents in addition to TDMA-heparin and BAC-heparin as mentioned in the examples below can also be incorporated into the base coat.

EXAMPLE 1

This example illustrates the immobilization of an anti-thrombogenic material (e.g., TDMA-heparin) onto a support member of the present invention. A base coat formulation consisting of the following chemicals were added into 15 ml toluene: 0.22 grams (g) of tridodecylmethlyarnmonium-heparin (TDMA-heparin), 1 g of Henkel 12-892 urethane-acrylate, 0.08 g of benzophenone, and 0.08 g of hydroxycyclohexyl phenyl ketone. Electrically polished 5 mm×25 mm stainless steel (SS) coupons were immersed into the solution. After air-drying for thirty minutes, the coupons were UV cured for eight minutes. One coupon was then dipped into 0.01% toluidine blue and rinsed with excess water. The color of the coupon turned light purple, indicating the existence of heparin. The heparin impregnated coupon was immersed into 2 ml of reconstituted bovine plasma and included an exchange of plasma every twenty-four hours. After a time period of forty-eight hours, no color was detected in the toluidine blue assay, indicating most heparin was eluted from the coating. The control coupon coated with the above formulation, except without TDMA-heparin, showed no color change in the toluidine blue assay.

EXAMPLE 2

This example illustrates the immobilization of an anti-thrombogenic material (e.g., benzalkonium-heparin) onto a support member of the present invention. A base coat formulation of the following chemicals were added into 15 ml AMS (1665-Q, Techspray Inc., TX): 0.22 g of benzalkonium-heparin, 1 g of Henkel 12-892 urethane-acrylate, 0.08 g of benzophenone, and 0.08 g of hydroxycyclohexyl phenyl ketone. Electrically polished 5 mm×25 mm SS coupons were immersed into the solution. After air-drying for thirty minutes, the coupons were UV cured for eight minutes. A coupon was then dipped into 0.01% toluidine blue and rinsed with excess water. The color of the coupon turned light purple, indicating the existence of heparin. The heparin impregnated coupon was immersed into 2 ml of reconstituted bovine plasma and included an exchange of plasma every twenty-four hours. After a time period of forty-eight hours, no color was detected in the toluidine blue assay, indicating most heparin was eluted from the coating.

EXAMPLE 3

This example illustrates the present invention using the base coat formulations from examples 1 and 2 to immobilize the anti-thrombogenic material (e.g., TDMA-heparin and BAC-heparin) onto a support member. Each of the base coat formulations from examples 1 and 2 were added with 1 g of cinnamaldehyde. Electrically polished 5 mm×25 mm SS coupons were coated in the solution and then UV cured as above. Next, 0.2 g of heparin (Sigma H-9266, ovine intestinal mucosa) was dissolved into 30 ml of distilled water. The pH of the solution was adjusted to 8.0 by adding 0.1 N KOH. The Schiff base coupling reaction was carried out at 55° C. for eighteen hours. An elution study was performed in bovine plasma similar to examples 1 and 2 above. The toluidine blue assay was performed at different time points. The table below summarizes the results:

| Coating | Color at t = 0 | Color at t = 24 hr | Color at t = 72 hr |
| --- | --- | --- | --- |
| PU-acrylate coated SS coupon | Silver | Silver | |
| Example 1, TDMA-heparin embedded | Light Purple | Silver | |
| Example 2, BAC-heparin embedded | Light Purple | Silver | |
| Example 3, TDMA-heparin embedded + heparin coupling on surface | Lighter Blue | Same as t = 0 | Lighter than t = 0 |
| Example 3, BAC-heparin embedded + heparin coupling on surface | Blue | Same as t = 0 | Lighter than t = 0 |

EXAMPLE 4

This example illustrates the present invention by including a pegylation step prior to the immobilization of the anti-thrombogenic material (e.g., heparin) onto the device surface. A base coat formulation of the following chemicals were added together: 1 g of urethane-acrylate (Cognis 6892), 1 g (0.10-1.20 g) of a heterodi-functional monomer, 0.08 g of benzophenone, 0.08 g of hydroxycyclohexyl phenyl ketone, 0.20 g of cellulose acetate butyrate, 15 g of ethyl acetate, and 3 g of n-butyl acetate. The SS coupons were coated with the base coat formulation and then UV cured as above. The SS coupons were put into 1 ml of 4 mg/ml of PEG(NH$_2$)$_2$ with a pH of 8.5 (MW=3400 from Shearwater Polymer) at 55° C. for twenty hours. After the Schiff base reaction, the coupons were rinsed with water.

An 8 mg/ml heparin solution (Sigma H-9266, ovine intestinal mucosa) and 8 mg/ml EDC were prepared in pH=4 buffer. Next, 900 u/l of heparin solution and 900 u/l of EDC solution were added into a vial containing the pegylated coupon and reacted at room temperature for three hours. The coupons were then rinsed with water and dried. The heparin retention experiment was carried out by immersing the coated coupons into phosphorous buffer (pH=7.4) over an extended period of time (please refer to table below for time points). An anti-thrombin III (AT-III) binding assay was performed to access heparin activity on the surface. The table below summarizes the results:

| Sample | Average Heparin Activity, U/cm$^2$ | % Activity Remained |
| --- | --- | --- |
| Pegylated coupon, t = 0 | 0.15 | |
| PU base coat + PEG + Heparin, t = 0 | 0.26 | 100% |
| PU base coat + PEG + Heparin, t = 24 hr | 0.15 | 58% |
| PU base coat + PEG + Heparin, t = 94 hr | 0.09 | 35% |

The heparin reaction performed with or without the pegylation step worked, but the coupling efficiency was not significant. The coupling efficiency was improved by using N-desulfated heparin (available from Celsus Laboratory).

EXAMPLE 5

This example illustrates the present invention using the base coat formulation from example 4 wherein the PEGylated support member was reacted with an EDC and heparin solution. A solution was prepared containing 0.5 mg/ml of polyethylenimine (Aldrich) and 0.5 mg/ml of NaCNBH3 in a pH=4 buffer and further adjusted the pH to 6.7. The solution was added into a 2 ml vial containing an ACS Multilink TriStar™ (manufactured by Advanced Cardiovascular Systems, Inc., Santa Clara, Calif.) stent and reacted for seventeen hours at 55° C. The stent was subsequently rinsed with distilled water.

An 8 mg/ml heparin solution (Sigma H-9266, ovine intestinal mucosa) and 8 mg/ml EDC were prepared in pH=4 buffer. Next, 900 u/l of heparin solution and 900 u/l of EDC solution were added into a vial containing the pegylated coupon and reacted at room temperature for four hours. The coupons were then rinsed with water and dried. The heparin retention experiment was carried out by immersing the coated coupons into phosphorous buffer (pH=7.4) for an extended period of time. An elution study produced results similar to those in example 4. The coated stent was e-beam sterilized at a dose of 50 kGy. An AT-III binding assay was performed to access heparin activity on the surface. The table below summarizes the results:

| Time Point & Sterilization | AT-III Binding (units/stent) |
| --- | --- |
| No E-Beam, t = 0 | 0.4 |
| After E-Beam, t = 0 | 0.39 |
| No E-Beam, t = 24 hrs in saline | 0.2 |
| After E-Beam, t = 24 hrs in saline | 0.28 |

What is claimed:
1. A method for immobilizing an anti-thrombogenic material onto a coating deposited on a surface of an implantable medical device, the method comprising:
    preparing a base coat mixture for application to the surface of the medical device, the surface of the implantable medical device optionally coated with a primer layer;
    applying the base coat mixture to the surface of the medical device;

polymerizing the base coat mixture to form a base coat layer on the medical device, the base coat layer comprising chemically functional groups;

performing a reaction between the chemically functional groups of the base coat layer and excess amine-terminated material;

rinsing the base coat layer with water; and performing a reaction between the anti-thrombogenic material and amine-terminated material on the surface of the medical device;

wherein the amine-terminated material is amine-terminated hyaluronic acid or amine-terminated polyvinyl pyrrolidone.

2. The method of claim 1, wherein the reaction between the excess amine-terminated material and the chemically functional groups within the base coat layer runs for about eighteen to twenty-four hours at a temperature in the range of 15° C. to 80° C. and about pH 7.0.

3. The method of claim 2, wherein the excess amine-terminated material is amine-terminated polyvinyl pyrrolidone.

4. The method of claim 3, wherein the concentration of the amine-terminated material is about 0.01 mg/ml to 20 mg/ml.

5. The method of claim 1, wherein the anti-thrombogenic material is unfractionated heparin.

6. The method of claim 5, wherein unfractionated heparin is reacted with amine terminated material and a water-soluble carbodiimide on the surface of the medical device for the immobilization of heparin thereon.

7. The method of claim 6, wherein the reaction between unfractionated heparin and amine-terminated material with the water soluble carbodiimide on the surface of the medical device runs for about two to six hours at about room temperature and about pH 4.5 to 7.5.

8. The method of claim 1, wherein the anti-thrombogenic material is N-desulfated heparin.

9. The method of claim 8, wherein N-desulfated heparin is reacted with amine terminated material and a water-soluble carbodiimide on the surface of the medical device for the immobilization of heparin thereon.

10. The method of claim 9, wherein the reaction between N-desulfated heparin and amine-terminated material with the water soluble carbodiimide on the surface of the medical device runs for about two to six hours at about room temperature and about pH 4.5 to 7.5.

11. An implantable medical device comprising
a coating deposited on a surface of the implantable medical device, the coating comprising an anti-thrombogenic material attached to the coating by the method of claim 1.

12. The method of claim 1, wherein the excess amine-terminated material is amine-terminated hyaluronic acid.

* * * * *